United States Patent
Dooney (10) Patent No.: US 7,179,296 B2
(45) Date of Patent: Feb. 20, 2007

(54) PARTIALLY CONSTRAINED BALL AND SOCKET

(75) Inventor: Tom Dooney, Mahwah, NJ (US)

(73) Assignee: Howmedica Osteonics Corp., Mahwah, NJ (US)

(*) Notice: Subject to any disclaimer, the term of this patent is extended or adjusted under 35 U.S.C. 154(b) by 329 days.

(21) Appl. No.: 10/405,139

(22) Filed: Apr. 2, 2003

(65) Prior Publication Data

US 2004/0199257 A1    Oct. 7, 2004

(51) Int. Cl.
*A61F 2/32* (2006.01)

(52) U.S. Cl. .................................... 623/21.21

(58) Field of Classification Search .. 623/22.18–22.19, 623/22.28–22.29, 22.4–22.45, 23.11–23.14; 606/102
See application file for complete search history.

(56) References Cited

U.S. PATENT DOCUMENTS

| | | |
|---|---|---|
| 3,003,399 A | 10/1961 | Donner |
| 4,213,208 A | 7/1980 | Marne |
| 4,279,041 A | 7/1981 | Buchholz |
| 4,678,472 A * | 7/1987 | Noiles ..................... 623/23.4 |
| 4,714,477 A | 12/1987 | Fichera et al. |
| 4,770,661 A | 9/1988 | Oh |
| 4,798,610 A | 1/1989 | Averill et al. |
| 4,944,758 A | 7/1990 | Bekki et al. |
| 4,950,299 A | 8/1990 | Noiles |
| 4,960,427 A | 10/1990 | Noiles |
| 5,062,853 A | 11/1991 | Forte |
| 5,147,386 A | 9/1992 | Carignan et al. |
| 5,156,626 A | 10/1992 | Broderick et al. |
| 5,282,864 A * | 2/1994 | Noiles et al. ............ 623/23.43 |

(Continued)

FOREIGN PATENT DOCUMENTS

DE    93 12 150.4    10/1993

(Continued)

*Primary Examiner*—Eduardo C. Robert
*Assistant Examiner*—Annette Reimers
(74) *Attorney, Agent, or Firm*—Lerner, David, Littenberg, Krumholz & Mentlik, LLP (57) ABSTRACT

A provisional prosthesis used during trial fitting of a bipolar or unipolar joint prosthesis such as a hip acetabular component. The provisional prostheses include an outer provisional shell component having an interior part-spherical surface having an open end with at least one recess extending from said open end into said interior surface. An inner component, such as a head for femoral component, is provided which has a part-spherical outer surface for articulation with respect to the part-spherical inner surface. The outer surface has at least one recess aligned with a polar axis of the inner component and the outer component has an inner surface with at least one recess which can be aligned with a recess on the inner component. A locking assembly, including a pin, is provided which can be inserted into the aligned grooves to rotationally lock the inner and outer components together. In order to keep the inner component from disengaging with the outer component, the outer component has an inner part-spherical surface which extends beyond the equator and the inner component has a flat cord formed around the circumference thereof which has a diameter less than or equal to the diameter of the opening in the outer component so that the head component can be placed inside and rotated and be constrained within the outer component throughout the range-of-motion of the implant.

28 Claims, 8 Drawing Sheets

U.S. PATENT DOCUMENTS

| | | | |
|---|---|---|---|
| 5,549,681 A | 8/1996 | Segmüller et al. | |
| 5,725,591 A * | 3/1998 | DeCarlo et al. | 623/22.29 |
| 5,800,556 A * | 9/1998 | Sanders et al. | 623/22.45 |
| 5,989,294 A * | 11/1999 | Marlow | 623/22.16 |
| 2002/0116068 A1 | 8/2002 | McLean | |
| 2003/0050703 A1 | 3/2003 | Harris et al. | |
| 2003/0171817 A1 * | 9/2003 | Rambert et al. | 623/22.17 |
| 2004/0054421 A1 * | 3/2004 | McLean | 623/23.11 |
| 2004/0078083 A1 | 4/2004 | Gibbs et al. | |

FOREIGN PATENT DOCUMENTS

| | | | | |
|---|---|---|---|---|
| WO | WO 01/76511 | * | 10/2001 | 623/22.17 |
| WO | WO 01/76511 A1 | | 10/2001 | |

* cited by examiner

PARTIALLY CONSTRAINED BALL AND SOCKET

BACKGROUND OF THE INVENTION

The present invention relates to a set of provisional prosthesis instrumentation, and more particularly to instrumentation which is suitable for use in hip hemiarthroplastly procedures. In such procedures, the proximal portion of the femur is replaced with a suitable prosthetic hip joint implant or implant assembly which will mate or articulate directly with the natural acetabulum (as opposed to mating with a prosthetic acetabular joint implant component).

The present invention also relates to an articulated prosthesis comprising a first articulating portion having a part-spherical bearing surface for engaging the acetabulum and a second inner part-spherical articulation surface and a second articulating component having an outer part-spherical bearing surface adapted to engage the second inner part-spherical bearing surface of the first component. More particularly, the invention relates to a prosthetic hip joint comprising a component for contacting the acetabulum, including the part-spherical inner and outer bearing surfaces and a femoral component having a part-spherical head.

Artificial implants, including hip joints, shoulder joints and knee joints, are widely used in orthopedic surgery. Hip joint prostheses are the most common. The human hip joint acts mechanically as a ball and socket joint, wherein the ball-shaped head of the femur is positioned within the socket-shaped acetabulum of the pelvis. Various degenerative diseases and injuries may require replacement of all or a portion of a hip using synthetic materials. Prosthetic components are generally made from either metals, ceramics, or plastics.

Total hip arthroplasty and hemi-arthroplasty are two procedures well known within the medical industry for replacing all or part of a patient's hip. A total hip arthroplasty replaces both the femoral component and the acetabular surface of the joint, so that both a femoral prosthesis and an acetabular prosthesis are required. A conventional acetabular prosthesis may include a metal cup, a metal cup and a polyethylene liner, or in some cases only a polyethylene cup, all of which may be formed in various shapes and sizes. Generally, a metal cup and a polymeric liner are used. The liner may be made of a variety of materials, including ultra high molecular weight polyethylene and ceramic materials. The metal cup is usually of generally hemispherical shape and features an outer, convex surface and an inner, concave surface that is adapted to receive a cup liner. The liner fits inside the cup and has a convex outer and concave inner surface. The cup liner is the bearing element in the acetabular component assembly which engages the femoral component. The convex outer surface of the liner corresponds to the inner concave surface of the metal cup or the natural acetabulum, and the liner concave surface receives the part-spherical head of a femoral component.

In general, a bipolar prosthesis has an external surface which articulates with the natural acetabulum and an internal surface which articulates with the part-spherical head member of a prosthetic femoral component. Another type of prosthesis is referred to as a unipolar endoprosthesis in which the prosthetic femoral component includes a spherical head member which is large enough to articulate directly with the natural acetabulum. Both of the above hemiarthroplasty procedures enable articulation with the natural acetabulum. These two procedures permit later conversion to a total hip replacement in which the acetabular portion is also replaced with a prosthetic acetabular component. With the bipolar conversion procedure, the bipolar prosthesis is removed from the head of the hip stem, and an acetabular prosthesis implanted which mates with the head of the remaining femoral component. With the unipolar endoprosthesis, these may typically be modular (where the head is a separate component from the stem portion of the hip prosthesis). This permits the larger unipolar head to be removed and replaced with a smaller prosthetic femoral head to mate with an acetabular prosthetic implant component.

A number of methods are known for retaining the ball or part-spherical femoral head in the bearing surface of the acetabulum or socket. In the most common method, referred to herein as "semi-constrained" construction, the patient's own anatomy, i.e., his muscles, tendons and ligaments, are used to retain the ball within the socket. For this construction, a hemispherical socket typically is used which allows the ball and its attached arm, such as the neck of a femoral component, the maximum amount of movement without contact of the arm with the edge of the socket. The surgeon, when installing such a semi-constrained joint, aligns the ball and socket as closely as possible with the patient's natural anatomy so that the patient's movements do not tend to dislocate the ball from the joint. This requires precise alignment and in some cases the precise alignment is difficult to obtain. This is especially true when the primary or first artificial joint such as a prosthetic hip implantation has to be revised with the implantation of a second or revision implant.

In order to increase the inherent stability against dislocation of such semi-constrained constructions, it has become conventional to add a cylindrical portion to the hemispherical socket to make it deeper. Although the ball is not physically constrained by the socket, by this adjustment the ball does have further to travel than if just a hemisphere had been used and thus some reduction in the propensity towards dislocation is achieved. Ball and socket joints of this type generally provide an arc or range-of-motion of approximately 115° when a 28 mm diameter sphere is used for the head of, for example, the femoral component and then the socket or bearing component is made a few millimeters deeper than a hemisphere. Larger ranges-of-motions can be obtained by keeping the size of the neck or arm attached to the ball constant and increasing the diameter of the ball. In this way, the angular extent of the arm relative to the ball becomes smaller. In the limit, if the ball could be made progressively larger and larger, a range-of-motion of 180° could be achieved.

One problem with artificial joint implants, such as hip implants, is that there is a very small percentage of hip joint implant procedures using the semi-constrained construction which dislocate. Such dislocations essentially make the patient immobile and can necessitate a second operation.

An alternative to the semi-constrained construction is a construction wherein the ball is physically constrained within the socket. In this construction, the part-spherical acetabular cup includes an extension which extends beyond the equator of the cup. Since the bearing encompasses more than one-half of the ball, the bearing thus constrains the ball from dislocation. Alternately, if the bearing is made of plastic, such as ultra-high molecular weight polyethylene (UHMPWE), the ball and bearing may be assembled by forcing the bearing over the ball. Obviously, the more the ball is surrounded by the bearing, i.e. the greater the latitude below the equator which the bearing extends, the more difficult it is to insert the head or ball of the ball and socket joint. In addition, the more that the bearing encompasses the ball, the smaller the range-of-motion for the ball prior to contact of the bearing with the neck or arm attached to the ball.

U.S. Pat. No. 4,960,427 to Douglas G. Noiles, relates to a constrained ball and socket joint for implantation in the hip. The design requires a multitude of parts in order to accomplish the constrained relationship between the ball of the femoral component and the bearing socket of the acetabular component.

U.S. Pat. No. 4,770,661 to Indong Oh, relates to a cup assembly having an insert or bearing within the cup and a locking ring at least partially within the cup. The locking ring has a conical surface that mates with the conical surface of the head with the assembly held together by fastener means, such as screw threads, on the locking rings and the cup.

U.S. Pat. No. 5,062,823 to Mark Forte, relates to a prosthetic hip joint for including an acetabular cup with a split ring for retaining the femoral head in the bearing. The split ring includes an upper split locking ring with a section for sliding within a guide in the bearing of the acetabular component. After assembly, the locking ring slides distally to lock the head of the femoral component in the acetabular cup.

U.S. Pat. No. 5,156,626 to Broderick et al., relates to instrumentation to be utilized with a trial bipolar hip prosthesis. The instrumentation includes two inner components to be used with an outer hemispherical bearing component with one component allowing rotation of a femoral head within the inner component, thereby producing a bipolar hip implant and wherein the second inner component allows the outer bearing component to be rotationally fixed with respect to the femoral component, thereby producing a unipolar hip implant. A plurality of sizes for the three components may be provided.

There has also been a long felt need to provide a means of converting a trial or provisional bipolar prosthesis into a unipolar trial prosthesis. Such a trial system includes an inner component and an outer component with the inner component comprising a substantially hemispherical exterior surface adapted to operatively engage a substantially hemispherical inner surface on the outer component. If the components are to be used in a hip joint, the outer component has a substantially hemispherical exterior surface for engaging the acetabulum. The inner component is connected to or integral with, in the case of a hip arthroplasty, a femoral component at its proximal end. Normally, this head portion is the inner component of the provisional or trial system.

In use, the trial can act as a bipolar hip prosthesis in which the inner component articulates with respect to the outer component and the outer component articulates with respect to the acetabulum.

As shown in U.S. Pat. No. 5,156,626 a second inner component is necessary to convert the trial bipolar prosthesis to a trial unipolar prosthesis. The inventor herein has developed a locking element which can be inserted into aligned grooves in the inner and outer components, thus changing the bipolar prosthesis into a unipolar prosthesis since pins of the locking element can engage the aligned grooves and prevent the relative rotation of the outer component with respect to the inner component.

The system of the present invention can be designed to eliminate the necessity of removing a modular head from, for example, a femoral component and replacing it with a modular head of a different design such as shown in U.S. Pat. No. 5,156,626.

In addition, it is desirable to preclude the trial head or inner component from disengaging from the trial outer component during this procedure. To accomplish this, a recessed portion or flattened portion is located intermediate spherical portions of the part-spherical inner component with the spherical inner surface of the outer component extending beyond the equator thereof to a diameter at its open end less than the diameter of the outer circumference of the part-spherical surfaces of the inner component or head but larger than the recessed portion so that the recessed area of the inner component or head may be aligned with the smaller outer component diameter and passed therethrough during insertion. The flattened portion may be oriented on the head at angles anywhere between perpendicular and coaxial with the polar axis of the inner component. When the inner component or head is rotated so that a conical recess therein may be attached to a conical trunnion on, for example, a femoral component, and the recessed or flattened area on the head circumference is at an angle wherein it can no longer be aligned with the open end diameter of the outer component, the trial head is captured within the assembly. In this embodiment, the head can still include grooves which can be aligned with grooves in the outer component so the assembly can be converted from a bipolar hip prosthesis to a unipolar hip prosthesis.

While the constraining system described herein is taught in connection with a trial prosthesis, such could be utilized in an actual prosthetic implant where it is desirable to ensure that the head does not disengage from the acetabular component. The implant can be of any type used to replace a ball and socket joint such as a hip or shoulder.

SUMMARY OF THE INVENTION

It is an object of the invention to provide a simplified method of converting a bipolar trial prosthesis to a unipolar prosthesis.

It is a further object of the invention to provide a kit of trial prosthetic hip implants which can be used either in bipolar or unipolar hip implantations.

It is yet a further object of the invention to provide a modular femoral trial or implant head component which can be captured within the bearing component of an acetabular trial or implant at least at the extremes of the rotational range-of-motion of the prosthetic hip implant with respect to the prosthetic acetabular implant.

These and other objects are achieved by a provisional prosthesis for use during trial fitting of a bipolar or unipolar joint prosthesis, such as a hip prosthesis used in total arthroplasty, which trial or provisional includes an outer component having an interior part-spherical surface having an open end with at least one open recess or groove extending from the open end and into the part-spherical surface. The groove is open to the interior surface of the outer shell component. An inner component, such as a trial femoral component head, is provided having a part-spherical outer surface for articulation with respect to the part-spherical interior surface of the outer component. The outer surface of the inner component has at least one recess open to its outer surface which recess can be aligned with the recess in the outer component. A locking assembly is provided which includes at least one pin for insertion into the aligned recesses or groove of the inner and outer components. The pin engages the aligned grooves and prevents relative rotation between the inner and outer components.

In the preferred embodiment, the groove extends generally parallel to the polar axis of the part-spherical surfaces.

If the inner component is a modular head adapted to be fixed on a conically tapered trunnion on the hip or femoral implant then preferably the grooves extend parallel with the central axis of femoral component trunnion which normally is coaxial with the polar axis of the inner or head component. In the preferred embodiment, each of the inner and outer components have at least three alignable grooves around the circumference of the inner and outer components which grooves extend from an equatorial region of the part-spherical surfaces. The at least one open groove on the components obviously has to be open to the open end of the outer component to allow insertion of the locking assembly.

The locking assembly may include a circular base having at least one and preferably three pins extending outwardly therefrom for insertion into the aligned grooves of the inner and outer components. While the pin accepting grooves on the outer and inner component can be placed anywhere along the respective inner or outer surfaces thereof, preferably they are spaced equally around the circumference of the inner and outer components. Thus, if three pins spaced at 120° around the locking element are used the corresponding aligned grooves would be spaced at 120° around the circumference of the inner and outer components. Normally, the inner component includes a conically tapered cavity for receiving the typical conically tapered trunnion of a prosthetic component located in the medullary canal such as a femoral component. In order to hold the locking element pins in the aligned grooves, the pins may include split and outwardly biased free ends which are compressed upon insertion into the aligned grooves to thereby hold the locking element in position. In one preferred embodiment, the ends of these pins have a slot with an enlarged tip which compresses the slot during insertion into the aligned groove to develop a holding force.

In order to ensure that the inner component does not become disengaged from the outer component during the testing of the range-of-motion of the trial joint, the inner component, such as a prosthetic head for a femoral component, which includes a part-spherical outer bearing surface for slidably engaging the inner bearing surface of the second component, which may be an "endo" acetabular component has a cylindrical recess portion. The preferred inner component or head also has a conical bore for coupling the head to a coupling element or trunnion on the first component. As stated above, the head or inner component outer bearing surface has spherical portions separated by a cylindrical portion having a recessed diameter less than the spherical diameter or one or more chordal flattened portions extending around the circumference of the head component portion. The recessed portion has a maximum diameter of less than or equal to the smallest diameter of the opening of the outer component for receiving the head or inner component. The outer component, with its part-spherical inner bearing surface has a portion of the opening extending beyond an equator of the inner bearing surface to a sector having a diameter less than the equator of the inner surface. Thus, the modular inner component or head may be rotated until the recessed circumferential area, which has a diameter less than the minimum diameter of the outer component opening is aligned with the outer component opening. The head or inner component may then be inserted and then upon rotation cannot be removed since the diameter of the part-spherical portions of the inner component are greater than the diameter of the opening on the outer component.

When a femoral component is used, the coupling element on the head or inner component is preferably a conically tapered trunnion at the proximal end of the femoral component which is adapted to engage a corresponding conically tapered bore in the inner component or head of the femoral component. In this case, the central axis of the trunnion is coaxial with the polar axis of the inner or head component.

The recessed portion of the inner component or head may be cylindrical and may extend circumferentially around the inner component or head outer surface and be oriented at less than or equal to 90° with respect to the polar axis of the part-spherical surface. In other words, the recessed portion, which may be in the form of a flat, i.e., part cylindrical surface defined by a cord connecting the two spherical portions of the inner component. The recess, if cylindrical, may have an axis of rotation coincident with the polar axis of the component (90°) or may be perpendicular to the polar axis of the component. The recessed area could also be oriented at an angle of 0 to 90° around the cup inner surface by, for example, orienting the axis of the cylinder at 0 to 90° to the cup polar axis. Thus, when the inner component is inserted within the outer component, any movement from the aligned insertion position will lock the inner component within the outer component. The opening of the outer component which receives the inner component may have a cylindrical surface extending from the opening where the inner component is introduced into the interior of the cavity and intersecting with the inner spherical surface. The circumferential extent of the recessed circumferential portion is greater than the 180° and up to 360° about the outer circumference of the inner component.

These and other objects and advantages of the present invention will become apparent from the following description of the accompanying drawings, which disclose several embodiments of the invention. It is to be understood that the drawings are to be used for the purposes of illustration only and not as a definition of the invention.

DETAILED DESCRIPTION

Figure 5:
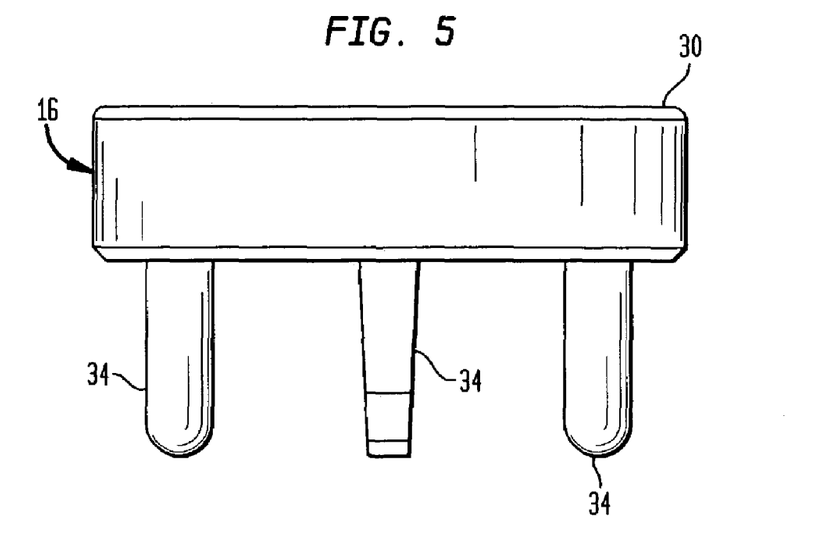
FIG. 5 is a side view of the locking element of the present invention.
Figure 6:
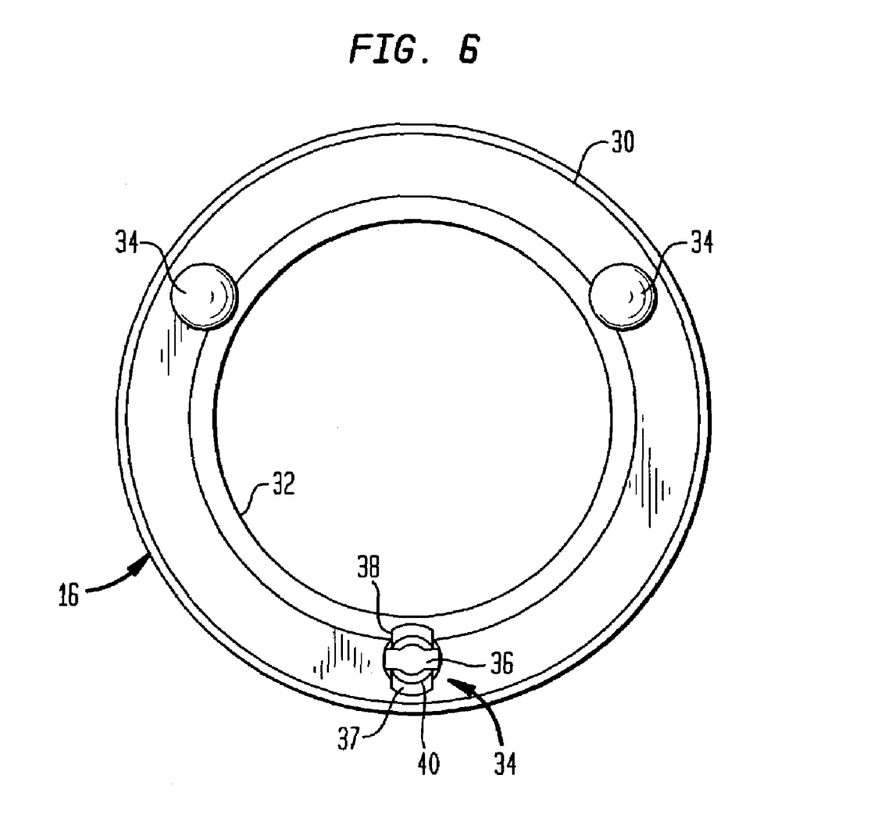
FIG. 6 is a top view of the locking element of the present invention.
Figure 7:
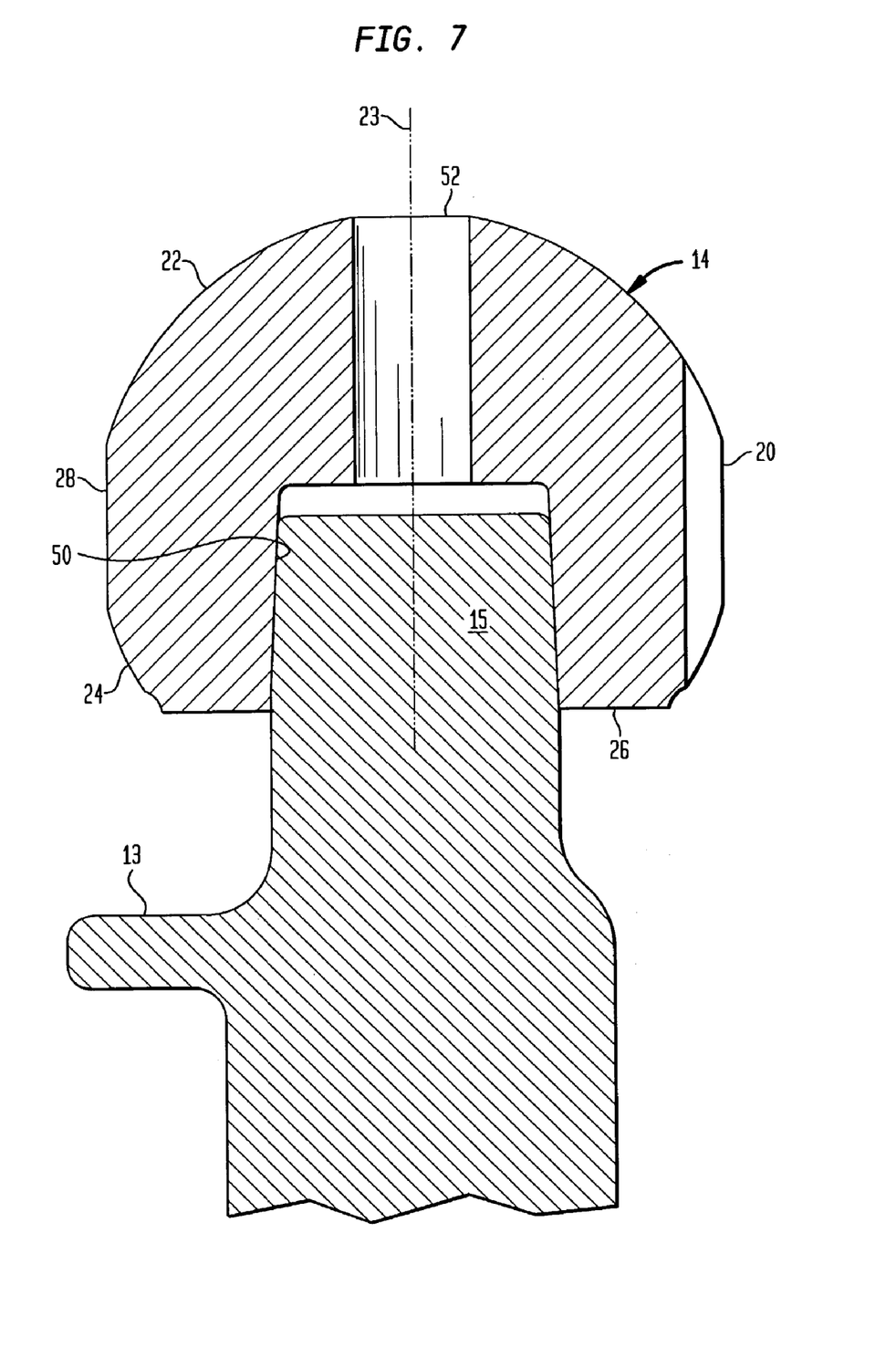
FIG. 7 is a cross-sectional view of the inner component of the present invention.

Referring to FIGS. 1–7 there is shown an exploded view of the device of the present invention which is utilized as a provisional head of a joint prosthesis. The device, generally denoted at 10, comprises a provisional or trial acetabulum contacting component 12, an inner component 14 and a locking element 16. In the preferred embodiment, the device 10 and inner component 14 is utilized in connection with a bipolar or unipolar hip implant which, as shown in FIG. 7, includes a femoral component 13 including a trunnion 15. Inner component 14 includes an opening 18 for receiving trunnion 15 of femoral component 13. In the preferred embodiment, the inner component 14 includes one or more grooves 20 extending parallel to the polar axis 23 of inner component 14. In the preferred embodiment, a series of three grooves 20 are used which are equally spaced around the circumference of inner component 14 and are thus are spaced at 120°. In the preferred embodiment, inner component 14 includes a part-spherical surface 22 which, in the case of a hip, is the proximal-most surface of the inner or head component. A second part-spherical surface 24 is located at the distal end 26 of inner component 14. In the preferred embodiment, surfaces 22 and 24 are separated by a recessed or flattened surface in the form of a cylindrical surface 28 which is formed around the circumference of inner component 14 by a chord connecting surfaces 22 and 24. In the preferred embodiment, the axis of cylindrical surface 28 is co-axial with axis 23. The function of surface 28 will be explained herein below.

Figure 1:
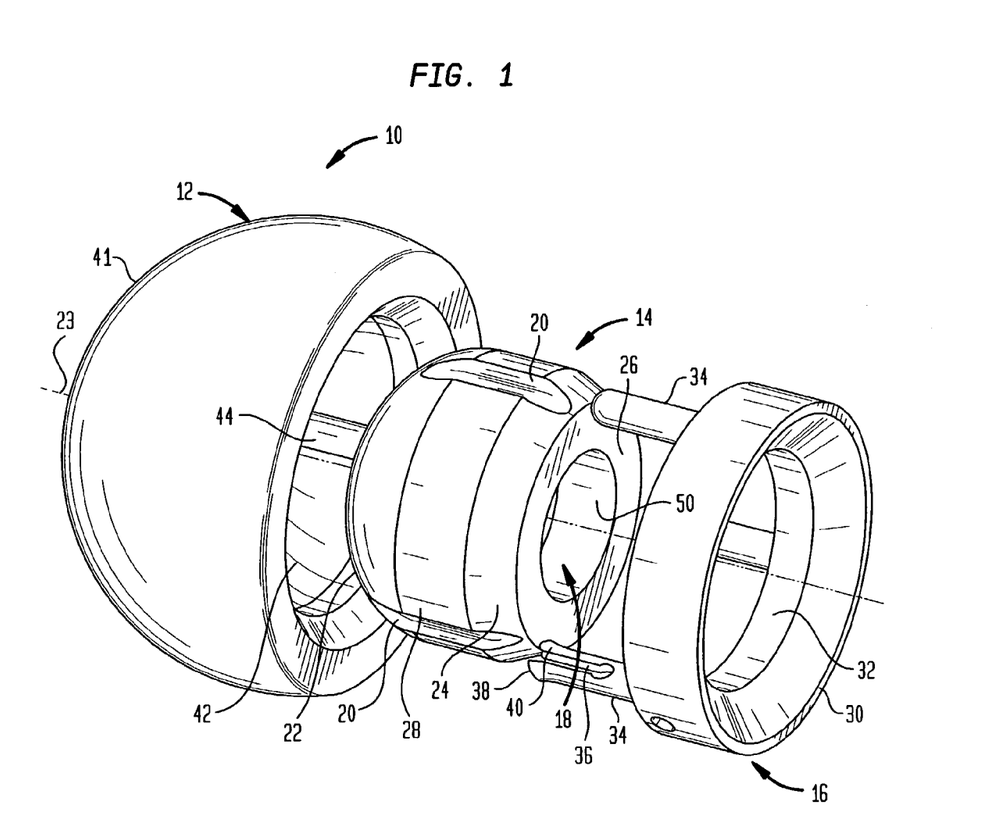
FIG. 1 is an exploded isometric view of the device of the present invention prior to the assembly of the inner component to the provisional shell to produce a bipolar joint prosthesis and prior to insertion of the locking assembly which converts the bipolar prosthesis to a unipolar prosthesis.

Locking element 16 includes a base 30 having an opened interior 32. In the preferred embodiment, locking element 16 includes three pins 34 which are alignable with the grooves 20 of inner or head component 14. In the preferred embodiment, one of the pins 34 includes a bifurcation formed by a slot 36. Slot 36 separates a pair of arms 38 and 40 which, in the preferred embodiment, have a widened tip 37. Alternatively, the arms 38 and 40 surrounding slot 36 can be outwardly flared.

Outer provisional or trial component 12 includes an outer spherical surface 41 and an inner spherical surface 42. In the preferred embodiment, outer spherical surface 41 is adapted to engage the natural acetabulum. Also in the preferred embodiment the inner surface 42 includes three grooves 44 which are alignable with the grooves 20 of inner component 14 and, when aligned, permits insertion of the pins 34 of locking element 16.

Figure 2:
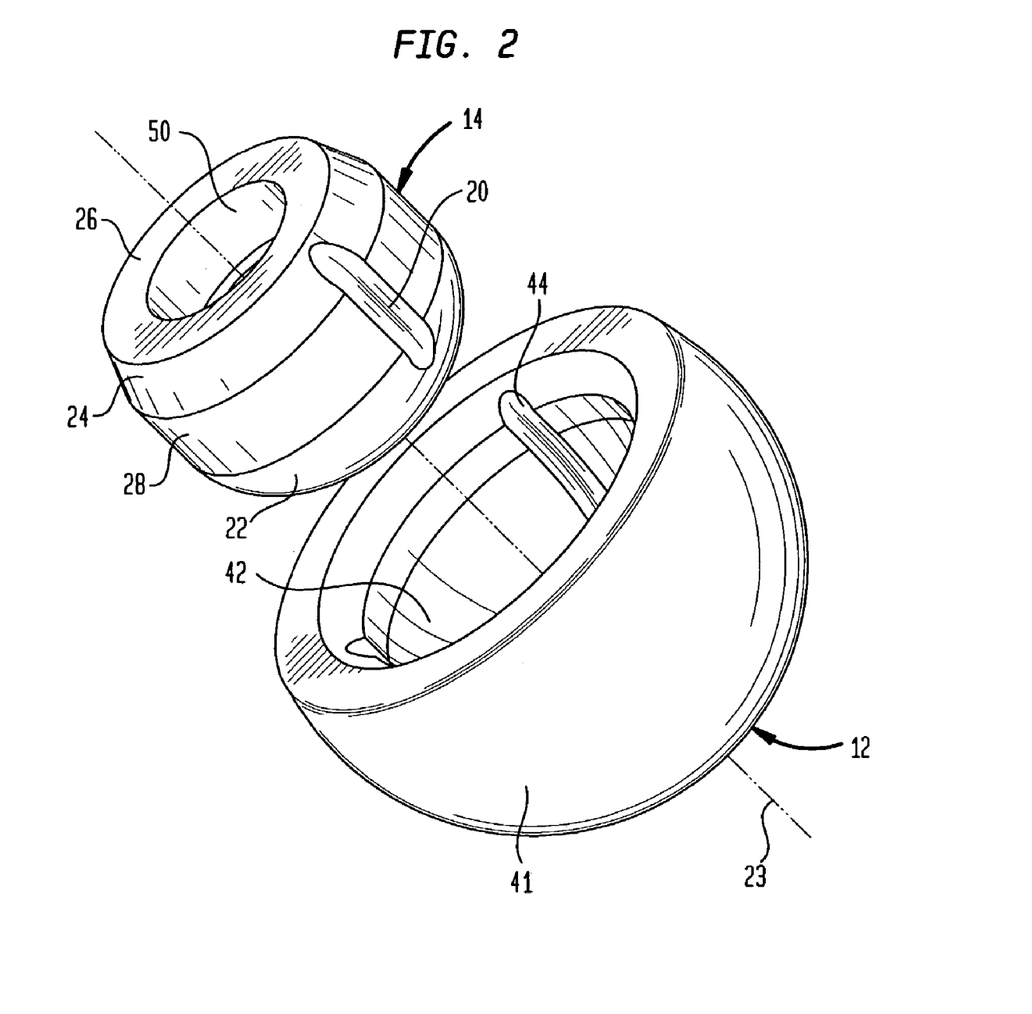
FIG. 2 is an exploded view of the inner and outer provisional components shown in FIG. 1.

Referring to FIG. 2 there is shown an exploded view of outer component 12 and inner component 14. Inner component 14 is inserted into inner surface 42 of outer component 12. The components are sized such that outer spherical surfaces 22 and 24 of inner component 14 are rotatable on spherical surface 42 of outer component 12. Inner component 14 can be assembled to trunnion 15 of femoral component 13 either prior to or after insertion within outer component 12. As can be best seen in FIG. 7, the preferred inner component 14 includes a conical bore or recess 50 which is open to what would be the distal end 26 of the inner component when used as a trial in total hip arthroplasty. The conical bore 50 is tapered in the standard manner to receive a trunnion of a hip implant or trial. Inner component 14 may include a throughbore 52 which allows the insertion of a tool (not shown) which aids in the removal of inner component 14 from the trunnion of the hip stem. Bore 52 may be threaded to receive a threaded tool. However, in the preferred embodiment as shown, component 14 is solid. As can be seen in the cross-sectional view of FIG. 7, spherical portions 22 and 24 are separated by the cylindrical portion 28 which extends as a chord connecting the portions 22 and 24. A groove 20 is shown in cross-section on the right hand side of FIG. 7. As can be seen in FIG. 7, in the preferred embodiment, cylindrical surface or chord 28 is a surface of revolution having the same central axis 23 as the polar axis of part-spherical outer surfaces 22 and 24. The diameter of spherical surfaces 22 and 24, in the preferred embodiment, is approximately 1.024 inches. In the preferred embodiment, groove 20 is a semi-circular recess of a diameter of about 0.125 inches with the complimentary semi-circular recess on the inner surface of member 12 also having a diameter of 0.125 inches. Obviously in the preferred embodiment, pins 34 are cylindrical and have a diameter of 0.125 inches. The material of trial components 1, 14 preferably is a polymeric material preferably ULTEM® thermoplastic polymer. (ULTEM® is a registered trademark of the General Electric Company.)

Figure 3:
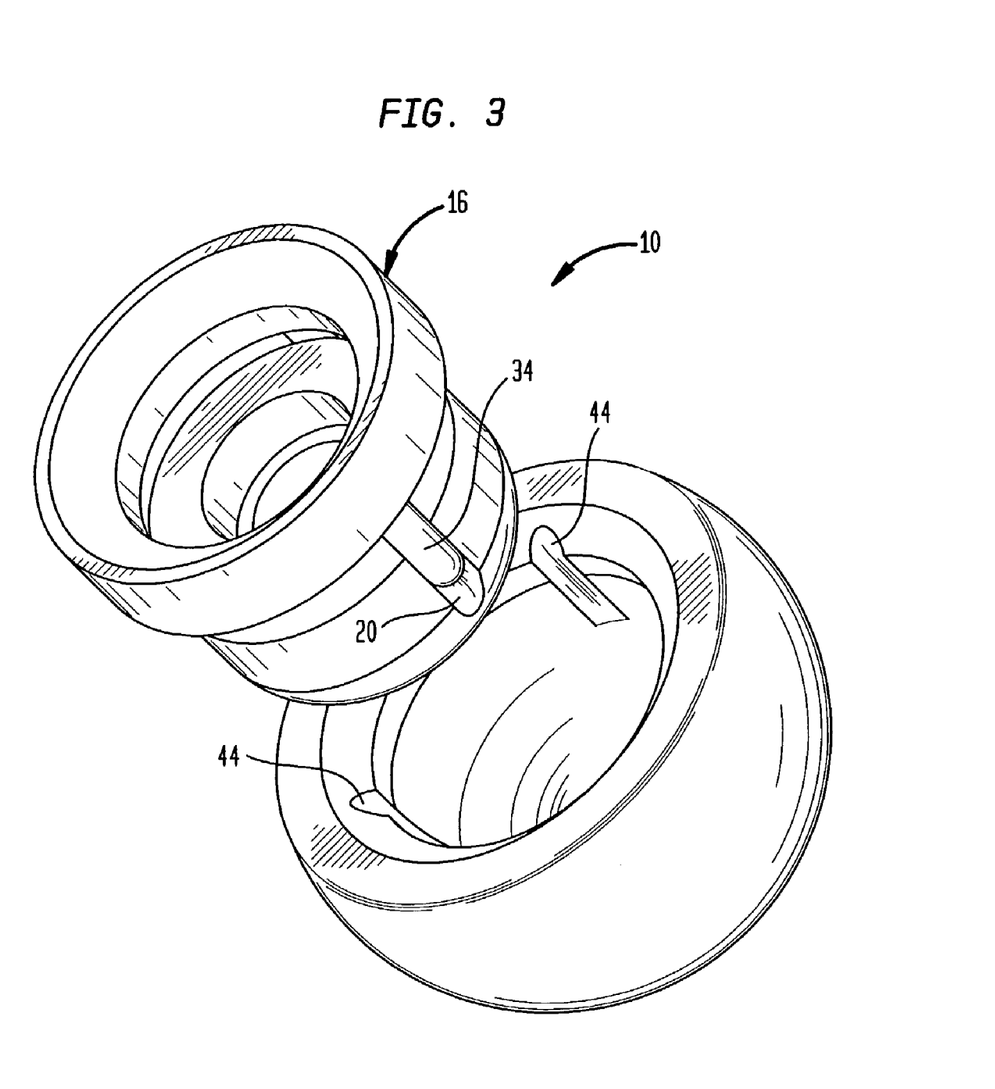
FIG. 3 is an exploded isometric view of the device shown in FIG. 1 with the locking element inserted into the grooves of the inner component.
Figure 4:
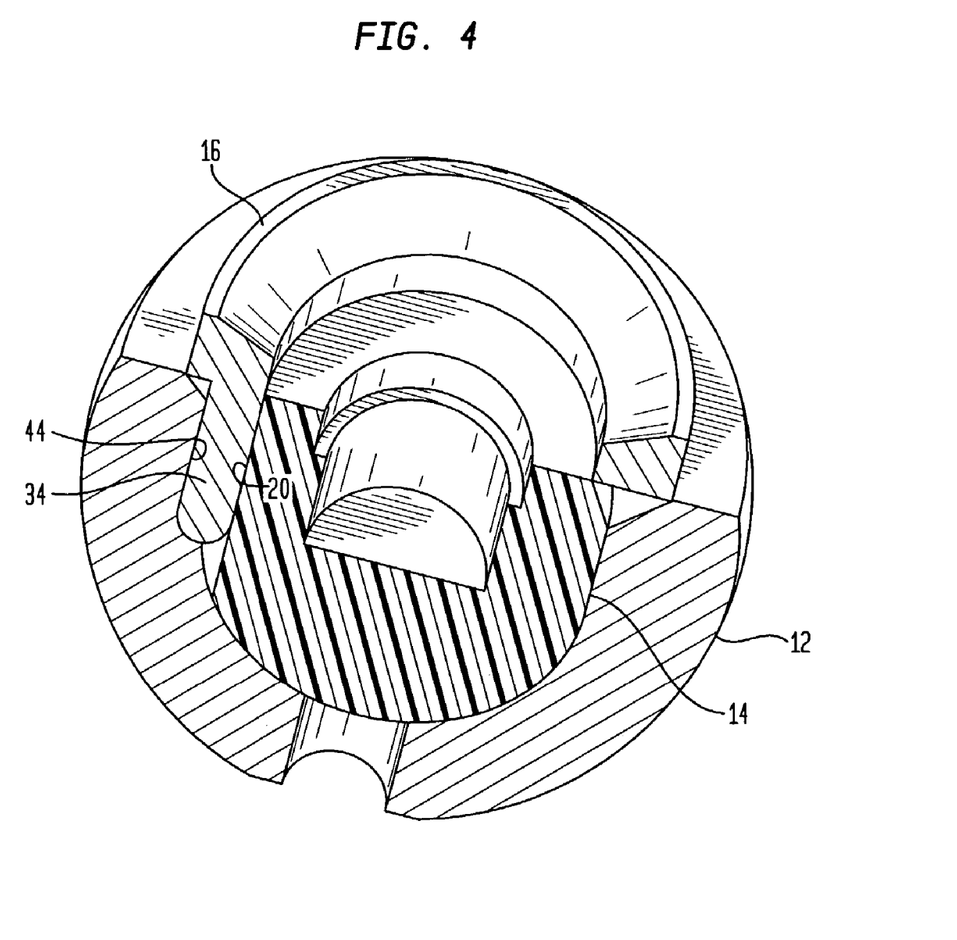
FIG. 4 is a cross-sectional view of the fully assembled device of the present invention with the pins of the locking element engaging with the inner and outer components.

Referring to FIGS. 3 and 4, there is shown the system 10 of the present invention being converted from a bipolar prosthesis to a unipolar prosthesis. The grooves of inner component 14 are aligned with the grooves of outer component 12 so that the pins 34 may engage the grooves 44 in the outer component 12. In this configuration, locking element 16 including pins 34 is then inserted into the combined grooves 20, 44 of the inner and outer components. The unipolar trial prosthesis in its fully assembled position is shown in cross-section in FIG. 4. Locking element 16 prevents any rotation between the outer component 12 and inner component 14 about the generally hemispherical surface 42.

Referring to FIGS. 5 and 6, locking element 16 is shown in elevation view and plan view, respectively. Referring to FIG. 5, pins 34 are shown extending outwardly from base member 30. Locking element 16 has a generally cylindrical surface 32 which engages the portion of spherical surface 24 immediately adjacent end 26 of inner component 14. In the preferred embodiment, there are three pins 34 equally spaced around locking element 16, i.e., at 120° increments. In the preferred embodiment, at least one of the pins 34 is bifurcated and is either inwardly deflectable into slot 36 or sprung outwardly so that upon insertion of the bifurcated pin the pin is somewhat compressed upon entering the combined recesses 20 and 44 so that locking element 16 can be more securely held therein. Of course, two or even three of the locking elements 34 may be split and/or flared outwardly to even more securely hold element 16 within the inner and outer components. The preferred locking element 16 is made of metal and is preferably machined metal.

Figure 8:
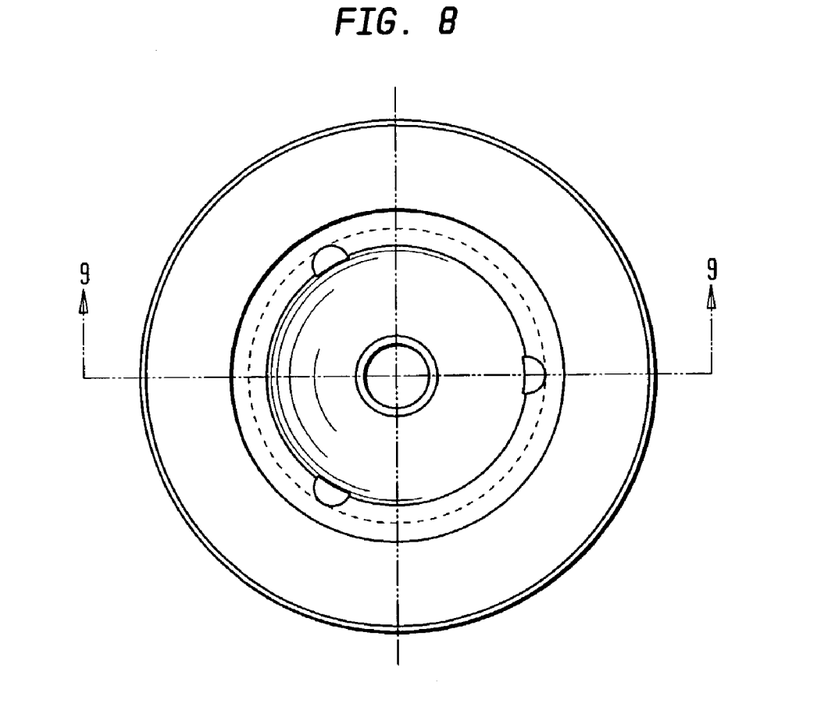
FIG. 8 is a bottom view of the provisional outer component of the present invention.
Figure 9:
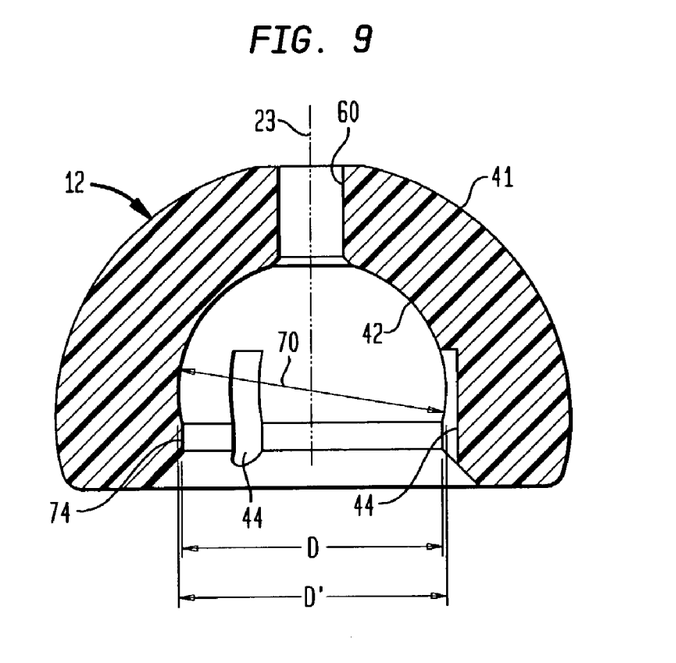
FIG. 9 is a cross-sectional view of the outer provisional component along lines 9—9 of FIG. 8.

Referring to FIGS. 8 and 9, there is shown in cross-section and in a bottom view, respectively, outer provisional or trial component 12. In the preferred embodiment, trial component 12 is made of a polymeric material such as preferably ULTEM® or other "polymeric" material and has a hemispherical outer surface 41 and a generally hemispherical inner surface 42. As discussed above, in the preferred embodiment, the inner surface 42 includes one or more grooves 44 which are semi-circular in cross-section and extend, as shown in FIG. 8, parallel to the polar axis 23 of the outer component. As discussed above in connection with the inner component, the grooves 44 of the outer component in the preferred embodiment are spaced at 120° increments so that they may be alignable with the grooves in the inner component. Obviously, fewer or more grooves 20, 44 may be utilized. However, the grooves in the inner and outer components must be alignable to the extent of the location of pins 34 on locking element 16. In other words, if locking element 16 has two pins 34 located at 180° from one another, at least two combined grooves in this location would have to be present on the inner and outer components. However, the inner and outer components could have four grooves spaced 90° from one another and still be usable with a locking element having a pair of pins 34 located at 180°. In the preferred embodiment, outer component 12 includes a bore 60 about polar axis 23 at its outermost surface. Bore 60 may be threaded and utilized to receive a tool for handling the component during use.

It should be noted that although in the preferred embodiment, the outer circumferential ring 30 of locking element 16 is a cylinder, it is possible in some cases to make an opening 30 in the manner of a split ring forming a space to allow the locking element 16 to be laterally slid onto the neck of a prosthetic femoral component or femoral component trial. The locking element 16 may then be slid proximally into engagement with, in the case of a hip implant, the aligned grooves 20, 44 of an assembled inner and outer component. This action would again convert a bipolar prosthetic implant or trial prosthetic implant into a unipolar implant but would not require the element 16, to be placed on the neck of implant 13 prior to insertion of trunnion 15 into outer component 14 and inner component 14 into outer component 12.

While the above description refers to a single outer component, inner component and locking element 12, 14 and 16, respectively, these items will normally be supplied in a kit with a variety of sized components. For example, outer components 12 may have outer diameters of 38 through 72 mm in 1 mm, 2 mm or 3 mm and 4 mm increments. If desired, the inner components and the inner diameter of the outer components may be kept at the same diameter throughout the range of increasingly larger outer components 12.

Figure 10:
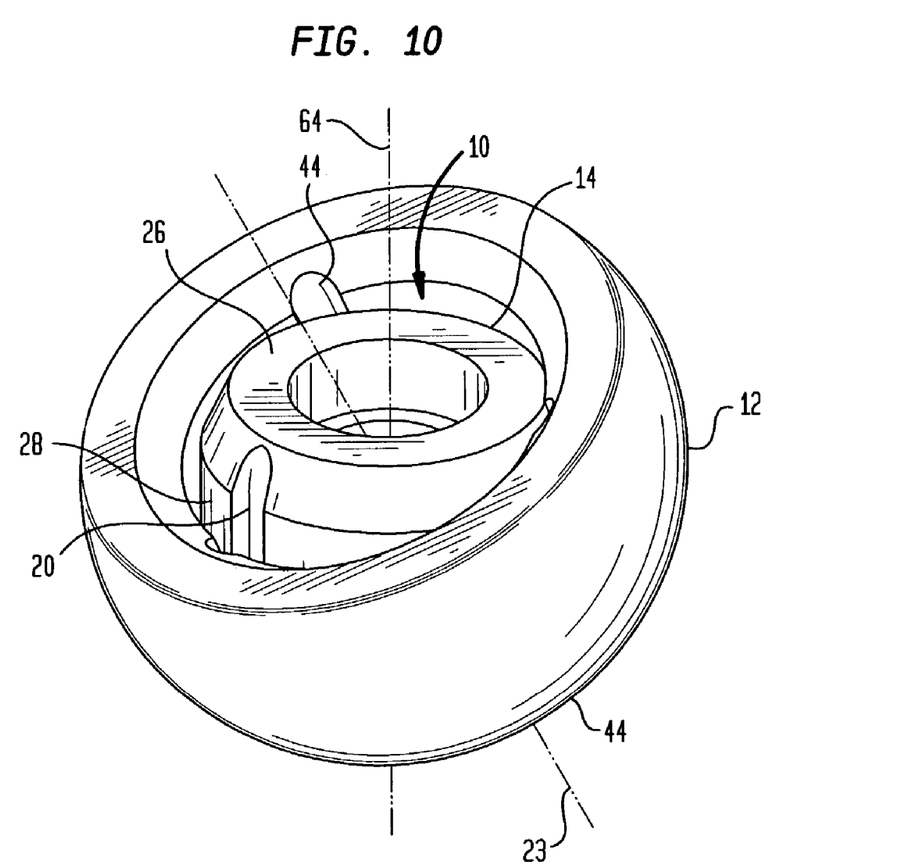
FIG. 10 is an isometric view of the inner provisional component captured within the outer provisional component.

Referring to FIG. 10, there is shown outer component 12 and inner component 10 in locking rotational engagement. The locking engagement is produced by the relative rotation of polar axis 23 of the inner component 14 and axis 64 of the outer component 12. As best seen in FIG. 9, the locking is produced by having the generally hemispherical inner surface 42 extend beyond the equator thereof to a diameter D which is less than the equatorial diameter D' of the spherical inner surface 42. In the preferred embodiment, at its open end, the inner surface of outer component 12 has a cylindrical surface 74 which extends from a diameter D below and consequently smaller than the equatorial diameter D' of the inner surface 42. In the preferred embodiments, cylindrical surface 74 may be 0.10 inches in length and have a diameter slightly greater than the recessed cylindrical diameter of the inner component 14. The recessed cylindrical diameter will then be less than the outer spherical diameter of the inner component 14 and thus prevent its removal once rotated. For example, the spherical surface of the inner component outer surface may be 1.024 inches while the diameter 70 of the inner spherical surface of the outer component may be 1.030 inches with the flattened portion 28 of head or inner component 14 being 0.99 inches and the cylindrical opening in outer component 12 being 1.0 inches. Parts are toleranced such that there can be no interference preventing assembly of the various components.

In the embodiments shown, when the polar axis of the inner and outer component are coaxial as shown in FIGS. 1–4, the inner and outer components can be assembled. After assembly, however, as soon as the polar axis are rotated with respect to one another, the larger diameters of surfaces 22 and 24 of inner component 14 can no longer pass through the opening of the outer component and the two parts are locked together. Of course in order to insert locking element 16, the polar axis of the inner and outer components would again have to be oriented in a coaxial manner. In the preferred embodiment, in order to disassembled the inner and outer components, the recessed or flattened portion 28 would have to again be correctly aligned with the opening in the outer components.

It should be noted that for a vast majority of positions during trial or, for that manner, during actual use after implantation, the inner and outer components of a bipolar hip prosthesis are not coaxially aligned. Thus, two parts as designed as shown in FIG. 10 and discussed above, would remain locked together as long as the axes 23/64 are not aligned. This could be further insured by locating the chord or flattened cylindrical surface at a latitude not coaxial with the polar axis of the head or inner component 14 which is not likely to be reached during use. The cylindrical portion 28 is preferably oriented at 90° to 30° with respect to polar axis 23 (FIG. 7 shows the 90° position). The circumferential cylindrical chordal portion 28 could even be oriented in a plane containing the polar axis (to the 0° orientation), i.e., rotated 90° from shown in FIG. 7 which would allow the head or inner component 14 to be inserted within the opening of the outer component 12 when rotated at 90° from that shown in the figures so that when the polar axis 23 and consequently the trunnion opening is rotated 90° to outer component axis 64. In this embodiment the inner component 14 must be mounted into outer component 12 prior to assembly on trunnion 15. In this position, when the inner component is aligned to accept trunnion 15 on femoral component 13, the inner and outer components 12, 14 would be locked together by the mismatch of the part-spherical surfaces 22 and 24 and the smaller opening of the outer component 12. The stem prevents the rotation of the head into a position wherein it can be disassembled. Thus, to remove the head it must first be disassembled from the stem. Such a design would prevent the uncoupling of the inner and outer components through any anticipated range-of-motion of the hip joint. Of course grooves 20 and 44 would be aligned so that the inner and outer components can be locked together when locking element 16 is engaged.

It should be noted that although the embodiment shown in FIG. 9 has been discussed in connection with a trial bipolar or unipolar prosthesis, such could be utilized with an actual bipolar or unipolar implant to prevent the inner and outer components from separating after implantation. Such a unipolar implant could be a typical prosthetic acetabular cup having a metal outer shell with a fixed polyethylene insert therein. The insert would have a part-spherical inner cavity shaped as discussed above in connection with outer component 12. The standard modular metal or ceramic head would be mounted on a prosthetic femoral component in a standard manner and be shaped as discussed above in connection with component 14. However, the grooves 20 and 44 would be eliminated since such are unnecessary in a typical prosthetic hip joint. In addition, the acetabular implant could be all polyethylene, i.e., without a metal outer shell but adapted internally as component 12.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A provisional prosthesis for use during the trial fitting of a bipolar or unipolar joint prosthesis comprising:
    an outer provisional shell component having an exterior and an interior part-spherical bearing surface defining a polar axis, said interior surface having an open end with at least one recess extending from said open end and open to said interior surface, said exterior surface for rotating on a natural joint surface;
    an inner component having a part-spherical outer surface defining a polar axis and a conical bore for receiving a tapered trunnion on a hip implantor trial, said inner component outer surface polar axis capable of free angular articulation with respect to said outer shell part-spherical interior surface polar axis towards an equator of said outer component part-spherical interior surface to form a plurality of angles between the polar axes, said outer surface having at least one recess open to said outer surface which can be aligned with said at least one recess in said outer component; and
    a locking assembly having at least one pin for insertion into said aligned recesses in said inner and outer component for preventing said free angular articulation between said inner component polar axis with respect to said outer component polar axis.

2. The provisional prosthesis as set forth in claim 1, wherein said recess in the inner and outer component is a groove extending generally parallel to a polar axis of said part-spherical surfaces.

3. The provisional prosthesis as set forth in claim 2, wherein said pin extends outwardly from a base member.

4. The provisional prosthesis as set forth in claim 2, wherein each of said inner and outer components have at least three alignable grooves extending from an equatorial region of said part-spherical surfaces.

5. The provisional prosthesis as set forth in claim 4, wherein said locking element base has three pins extending therefrom for insertion into each of said aligned grooves.

6. The prosthesis as set forth in claim 5, wherein said grooves are spaced equidistantly around the circumference of said inner and outer components.

7. The prosthesis as set forth in claim 6, wherein said inner component includes a cavity for receiving a trunnion of a prosthetic femoral component.

8. The prosthesis as set forth in claim 5, wherein one of said pins has a compressible free end for holding said pin in an aligned groove.

9. The prosthesis as set forth in claim 8, wherein said free end of at least one of said pins is slotted and has a pair of outwardly flared arms.

10. The prosthesis as set forth in claim 1 wherein the prosthesis is a hip or shoulder prosthesis.

11. A method of making a trial unipolar joint from a bipolar joint comprising:
    providing an implant with a conical male trunnion on a proximal end and a stem on a distal end into a bone canal, inserting an inner component onto said trunnion, said inner component having an open end and a conical bore for receiving said trunnion, said inner component having a part-spherical outer surface defining a polar axis with at least one recess formed in said outer surface; inserting said inner component into an outer component having an open end and an exterior part-spherical surface for contacting the joint for articulation therewith and a part-spherical inner surface defining a polar axis for receiving said part-spherical inner component for free mutual angular articulation of said polar axis of said part-spherical surfaces towards an equator of said outer component part-spherical inner surface to form a plurality of angles between the polar axes, said part-spherical inner surface having at least one recess formed thereon, said recesses open to said open ends of said inner and outer components;
    aligning said recesses on said inner and outer components; and
    preventing said mutual angular articulation between said inner and outer components by inserting a locking element having a base and a pin extending from said base into each of said aligned recesses, said pin having a cross-section generally conforming to a cross-section of said aligned recesses.

12. The method as set forth in claim 11, wherein said pins and recesses extend in a direction parallel to a polar axis of said part-spherical surfaces.

13. The method as set forth in claim 11, wherein said outer component inner surface has a portion adjacent said open end extending beyond an equator of the part-spherical surface to a diameter less than said equator.

14. The method as set forth in claim 13, wherein said inner component has two part-spherical outer surfaces separated by a recessed portion, said recessed portion having a maximum diameter less than or equal to said diameter of said outer component adjacent the open end thereof.

15. A joint prosthesis comprising:
    a first component having a conically tapered male trunnion on a proximal end thereof and a stem for insertion in a bone canal at a distal end;
    a second component having a part-spherical inner bearing surface, said surface having a portion extending beyond an equator of the part-spherical bearing surface to an open sector having a diameter less than said equator;
    a modular prosthetic head having a part-spherical outer bearing surface for slidably engaging said bearing surface of said second component, said head having a recessed conically tapered bore for coupling said head to the coupling element on said first component, said head bearing surface having spherical portions separated by a recessed cylindrical surface portion formed as a chord between the spherical portions extending as a surface of revolution about a polar axis of said head around a circumference of said head, said recessed portion having a maximum diameter less than or equal to said sector diameter of said second component.

16. The prosthesis as set forth in claim 15, wherein said coupling element on said first component is a trunnion having a conical outer surface.

17. The prosthesis as set forth in claim 16, wherein said recessed bore of said head is a conically tapered recess adapted to engage said trunnion on said first component, said conical outer surface and said conical recess formed about a central cone axis of said trunnion.

18. The prosthesis as set forth in claim 17, wherein said recessed portion is in a form of a cylinder centered on said cone axis.

19. The prosthesis as set forth in claim 17, wherein said head has a cylindrical portion extending circumferentially around said head outer surface along a surface oriented at $\leq 90°$ with respect to said cone axis.

20. The prosthesis as set forth in claim 19, wherein said cylindrical portion of said head is a flat circumferential surface in a form of a cord between adjacent spherical sectors.

21. The prosthesis as set forth in claim 20, wherein said flat circumferential surface is centered about said cone axis.

22. The prosthesis as set forth in claim 21, wherein the recessed circumference is oriented at 90° to the cone axis.

23. The prosthesis as set forth in claim 15, wherein said recessed portion of said head extends around a circumference of said head.

24. The prosthesis as set forth in claim 15, wherein said recessed circumference of said head is located within a latitude between 30° to 90° to said cone axis.

25. The prosthesis as set forth in claim 15, wherein said portion of said second component bearing surface part extending beyond said sector has a cylindrical shape.

26. The prosthesis as set forth in claim 15, wherein said outer bearing surface is part spherical and extends to at least the equator about a polar axis of said part-spherical bearing surface.

27. The prosthesis as set forth in claim 15, wherein said first component is a femoral component and said second part is an acetabular component.

28. The prosthesis as set forth in claim 15 wherein the first component is a humeral component and the second component is a glenoid component.

* * * * *